United States Patent [19]

Mattesky

[11] Patent Number: 5,098,713
[45] Date of Patent: Mar. 24, 1992

[54] CEDAR BLOCK ASSEMBLY
[75] Inventor: Henry Mattesky, Cedar Grove, N.J.
[73] Assignee: Herbert Glatt, Morristown, N.J.
[21] Appl. No.: 675,324
[22] Filed: Mar. 26, 1991
[51] Int. Cl.⁵ ............................................. A01N 25/34
[52] U.S. Cl. .................................... 424/412; 424/405; 424/409; 424/411; 424/DIG. 10; 223/86
[58] Field of Search ............... 424/412, DIG. 10, 405, 424/409, 411; 223/85, 86, 89, 90, 91; 512/4; 514/918, 919

[56] References Cited

U.S. PATENT DOCUMENTS

| | | | |
|---|---|---|---|
| 1,741,068 | 12/1929 | Newsom | 223/86 X |
| 3,688,985 | 9/1972 | Engel | 512/4 X |
| 4,768,686 | 9/1988 | Storti | 223/86 |
| 4,918,871 | 4/1990 | Widmann | 51/181 R |
| 4,920,096 | 4/1990 | Bedoukian | 512/5 |

Primary Examiner—Thurman K. Page
Assistant Examiner—Robert H. Harrison
Attorney, Agent, or Firm—Omri M. Behr

[57] ABSTRACT

A cedar block assembly for preventing insect damage to clothing. At least one garment-confrontable surface of the block bears a plurality of grooves which increase the surface area of the block exposed. The block may be affixed to hanging means which permit the block to be placed and maintained in proximity to clothes or portions thereof needing protection from insect damage.

9 Claims, 2 Drawing Sheets

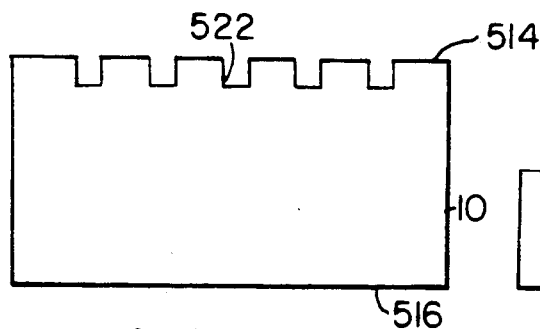
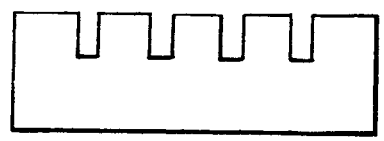
FIG. 4  FIG. 5
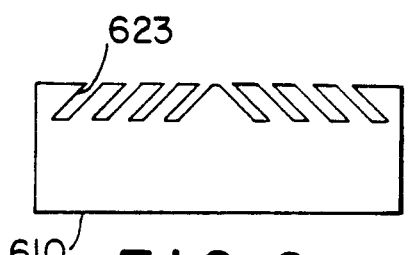
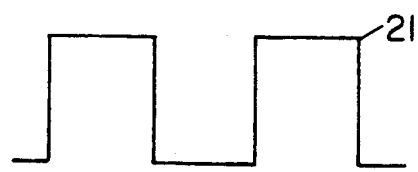
FIG. 6  FIG. 7
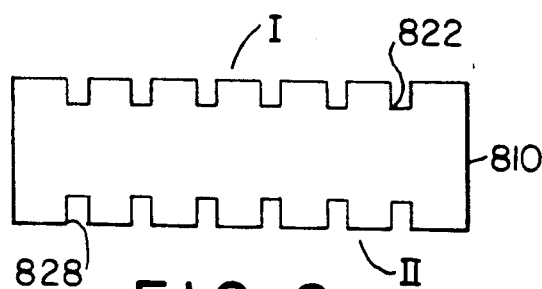
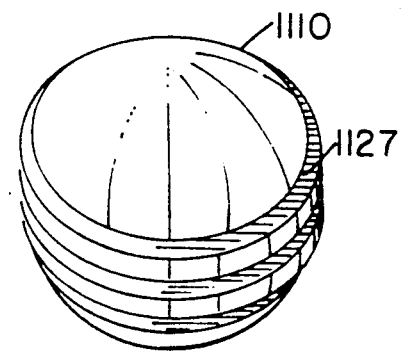
FIG. 8  FIG. 11
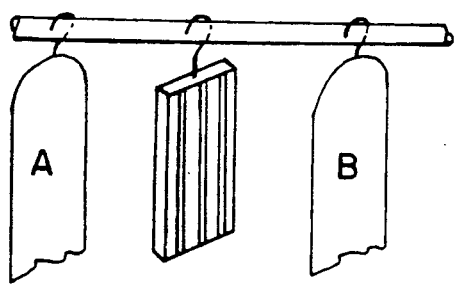
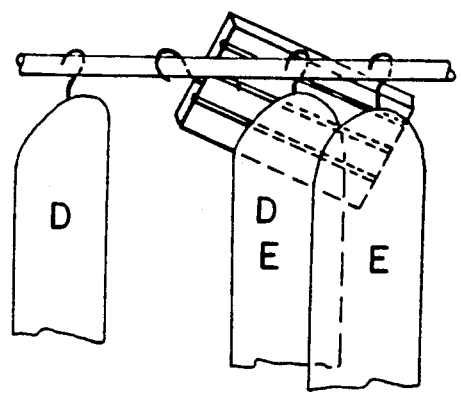
FIG. 9  FIG. 10

CEDAR BLOCK ASSEMBLY

FIELD OF THE INVENTION

This invention concerns an article of manufacture which provides natural scent for the protection and preservation of garments from damage by insect larvae.

BACKGROUND OF THE INVENTION

It is well known that certain insect larvae attack clothes which are in storage or in closets, especially clothes of woolen materials. Conventional ways of preventing this larvae damage have included packing clothes with mothballs, placing the clothes in a cedar closet, or storing the clothes with blocks made of cedar wood. Each of these solutions has serious drawbacks.

Mothballs, as is well known, have an unpleasant smell which clings to the clothes after they have been removed from storage. While cedar closets effectively prevent insect damage and impart a pleasant scent to clothes, such structures are expensive to construct and provide far more protection than is necessary. Thus, clothes which are not susceptible to attack by insect larvae, as well as woolen garments stored for short durations in cedar closets do not require the protection provided by such structures. As to simple blocks of cedar wood, it has been found that they are difficult to keep in place or to keep in proximity to woolen clothes or in the parts that are in need of protection. Instead, the blocks frequently fall out of place or to the floor of a closet, where their localized protection from insect larvae is of no use. The exuded vapor pressure falls to an unusable level after about 10–12 months.

Several approaches have been taken in the past to overcome the problem. Traversi, U.S. Pat. No. 989,448 disclosed a hollow garment hanger with a plurality of holes accessing an interim filled with cedar shavings. Travis, U.S. Pat. No. 1,863,511 discloses a base with holes containing cedar shavings. Farrel, U.S. Pat. No. 4,499,015 discloses vermiculite impregnated, inter alia, with cedar wood oil and cedar wood ketone in an open container. Recently, Widman, U.S. Pat. No. 4,918,871 attempted to overcome the vapor pressure drop problem by inserting an abrasive block in contact proximity to a cedar wood block to renew the exposed surface.

SUMMARY OF THE INVENTION

The cedar block assembly described in the instant application comprises a solid block suffused with cedar oil. At least one face of the block bears plurality of grooves which increase the surface area of the block exposed. The block can alternately be equipped with a hanging means which permits the block to be placed and maintained in proximity to clothes needing protection from insect damage. Slim, flat blocks are preferred, especially those having rounded or beveled outer edges, the grooves in the block are preferably parallel to one another and rectangular in cross-section. The blocks may however have irregularly spaced grooves, they may be substantially cubical, spherical, or even heart-shaped.

DESCRIPTION OF THE DRAWINGS

FIG. 4 is across-sectional view of FIG. 1 from 4—4. The cross-section of the grooves which is also illustrated is rectangular in shape in both figures.

FIG. 5 is a similar view to FIG. 4 but of a thinner block.

FIG. 6 is a cross-sectional view of a block when the grooves formed in the block are trapezoidal in shape.

FIG. 7 illustrates a detail of the cross-section of the grooves in FIG. 4.

FIG. 8 illustrates a block having grooves on two opposed sides.

FIG. 9, a cedar block assembly is suspended from a clothes closet bar and hangs between garments A and B.

In FIG. 10, a cedar block assembly is suspended to the rear of garments D and E which hang on a clothes closet bar.

FIG. 11 is a perspective view of a spherical embodiment of a block.

DESCRIPTION OF THE PREFERRED EMBODIMENTS

The cedar block assembly comprises a block material suffused with cedar oil and, if desired, a hanging means affixed to the block. The block may be comprised of a variety of materials. Certainly cedar wood itself is suitable. However, other woods which have been suffused with cedar oil under super-atmospheric pressure are also suitable for the assembly. Non-wood materials such as solid absorbent resins may also suitably be used.

Where items have more than two digits, items with common last two digits signify similar subject matter.

The block 10 in the assembly may be of any size. Given the desirability of a conveniently sized assembly which is portable and light-weight, as well as low price, a suitable size of the block is 30×10×1 cm. Preferred block sizes are within the dimensions of 6×6×1 to 2×2×2 cm. These sizes are suitable to scent all or part of a closet for a substantial amount of time, i.e., roughly one year, depending on the ambient heat and humidity. As to the shape of the block 10, any shape may suitably be used, however it is recognized that some shapes may be awkward in a clothes closet. Thus, when cubes, spheres or the like, are used for the block, the block may bump against closet walls and mark or dent them, since slimmer or flat blocks provide protection equal to that of these rounded or cubic blocks, it is preferred that the block shape be flat or slim. Thus, suitable preferred shapes include flat disks, flat rectangles 110 and flat ovals 210. However, the cubes 310 or spheres 1110 are suitable for insertion into shirts, sweaters and the like, which are stored horizontally in drawers.

Figure 1:
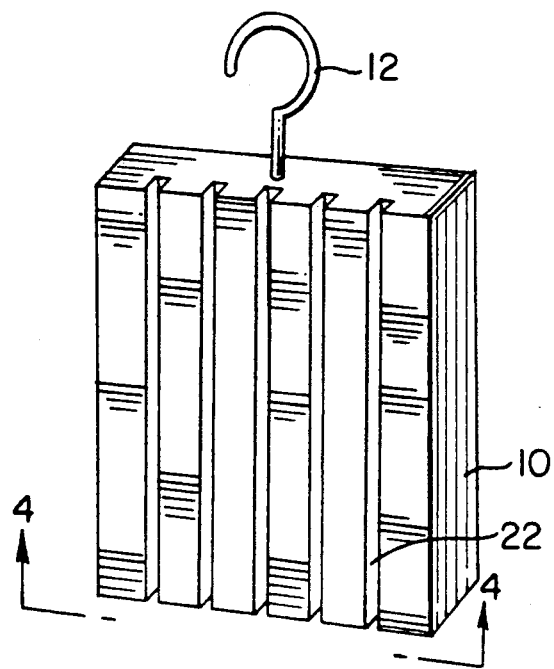
FIG. 1 is a perspective view of a cedar block assembly, one face of which bears parallel grooves; a hook is affixed to a top surface of the block.
Figure 2:
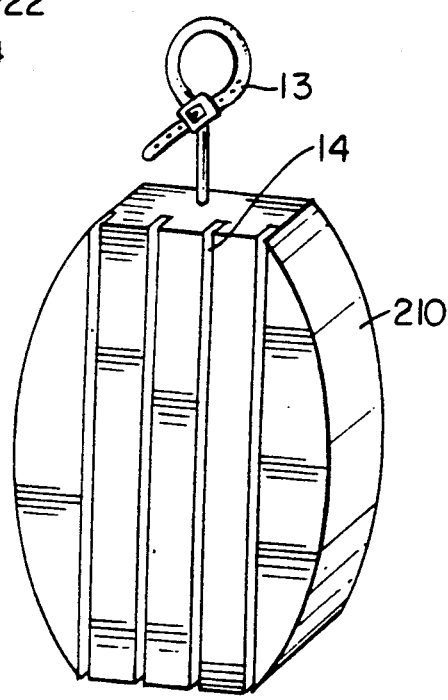
FIG. 2, the oval block assembly has an adjustable strap as its hanging means.
Figure 3:
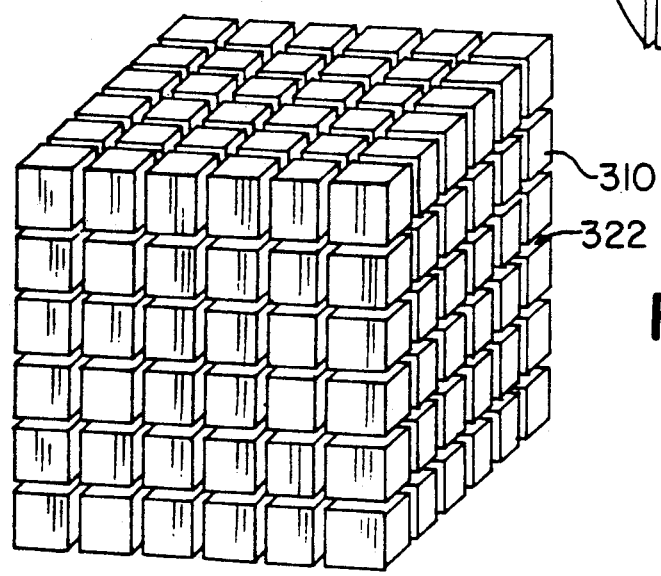
FIG. 3 illustrates a perspective view of a cubic block having cross-hatched grooves.

The block has at least one garment-confrontable surface. Where, as in FIG. 11 the block is spherical, it has a single surface 1110 the entirety of which may confront surrounding garments. Where the block has more than one garment-confrontable surfaces (as in FIG. 1–10), one or both of said surfaces may have grooves.

Where the block has a rectangular cross-section as in FIG. 1, the two opposed surfaces with the greatest surface area defined by the four corners of that surface are denominated major surfaces. (All remaining block surfaces are minor surfaces.) Preferably in such blocks, these major surfaces are also the garment-confrontable surfaces with one or both of said major surfaces bearing grooves (see FIGS. 1 and 4-5; and FIG. 8 respectively). Thus, block 10 in FIG. 1 in Applicant's Specification has one of its major surfaces bearing grooves 22, while the major surface on the reverse side of block 10 has no grooves, and all other remaining surfaces are minor and ungrooved.

Cubes are blocks of rectangular cross-section having six square faces each with equal surface area. In cubes, the "major" surfaces has an equal surface area to the "minor" surface: i.e., all surfaces may be said to be minor and major, and each has a surface area which is exactly 1/6 of the entire block surface area. In non-cubic blocks of rectangular cross-section, such as block 10 in FIG. 1, a major surface occupies more than 1/6 the entire surface area of the block. Thus, in all rectangular blocks, at least one major surface comprises at least 1/6 the entire surface area of the block.

It may be desirable that the edges of the block be rounded or beveled. Doing this, prevent snagging of the edges of the block on fabrics which are in the closet. While such rounding or beveling may reduce the amount of friction between the block and garments surrounding it, it must be recognized that friction from the block edges is less desirable than friction from the grooved faces of the block. This is because the block edge if sharp pointed, may pierce or snag the garment while the grooved surface merely prevents slippage of the garment with respect to the grooved face of the block.

Before discussing the suitable shape and size of the grooves 22,324,623,828,1127 to be made in the block, it is necessary to understand the three-fold purpose that these grooves serve. First, by increasing the surface area of the block, the grooves increase the amount of cedar oil which is volatilized and so increase the protection given to garments near the cedar block assembly. Second, by exposing part of the block deeper than the surface faces of the block, the grooves make accessible those amounts of cedar oil in the interior of the block. This increases the useful life of the cedar block assembly. Finally, the grooves provide means for retaining the block in proximity to the clothes needing cedar oil protection. Friction caused by rubbing of a garment against one or more of the grooves tends to retain the block in proximity to that garment.

Any shape of groove is suitable which accomplishes all three of the above purposes. It has been found that grooves having parallel sides 22,828,1127 are easiest to form as illustrated in FIGS. 4 and 5, although grooves with non-parallel sides 623 are within the scope of this invention.

The cross-sectional shape of the grooves in the block may be square, rectangular, trapezoidal 623 as in FIG. 6, or rounded at the bottom. Additionally, a groove narrowing from the face of the block down to the point at the bottom of the groove is suitable. While rounded grooves are suitable, it is desirable that the groove form a sharp edge 21 at the surface face of the block. This edge may be beveled but it is preferably not rounded off. This sharp edge at the top of the groove illustrated in FIG. 7 by element 21 is particularly important in providing frictional contact between the block and garments with which it comes in contact.

The depth of the grooves may be shallow or deep. It is important to note however that the grooves should not be so deep that they weaken the block size or those parts of the block between the blades. Shallow grooves can provide sufficient friction to retain the block in contact with garments needing protection. However, deeper grooves are preferable, i.e., greater than 1 mm. of an inch deep in order to expose greater amounts of block surface area and thereby volatilize those cedar oils present in the block interior.

Basically, any width of groove is suitable. The groove widths be from 1 mm. to 10 mm. wide. There is a danger which arises from grooves which are too narrow that insufficient friction will be generated with the garments. Conversely, if grooves are too broad, insufficient surface area of the block be exposed to provide a block with long useful life. A preferred range of groove widths is from 1 to 3 mm. wide.

Just as groove width is important, so is the spacing between the grooves, it is preferred that the space between grooves be at least 1 mm. in order to impart sufficient strength to those parts of the block between the grooves. It is also preferred that one groove not be separated by more than 10 mm. from any other groove or group of grooves. This is because such wide spacing of grooves would fail to expose sufficient surface area of the block. It is noted that grooves may be grouped in one or more pluralities. By doing so, the block may be given a decorative and attractive appearance.

As to the number of grooves on the block, any number of grooves more than one is suitable, it is recommended however that a substantial portion of at least one surface of the block be covered with a plurality of grooves. Preferably, no block has fewer than three grooves.

As noted briefly above, grooves may be placed on the block in patterns which impart a decorative and attractive appearance on the block. This may be done as noted by grouping one or more grooves together in several groups. It may also be done by placing several types of groove on the block face. Thus, any one block may have more than one of the following groove types: round bottom, square bottom, parallel sided, or non-parallel sided. Moreover, each groove need not be parallel to the other grooves, thus cross-hatchet patterns of grooves may be desirable (see FIG. 3). As with the width and spacing of the grooves, it should be noted that in forming groove patterns, one should take care not to weaken the block size or those parts of the block between the grooves.

So far this discussion has considered grooves to be present only on one face of the block. It is noted that the present invention comprises cedar block assemblies having grooves on at least one face. Therefore, grooves may be present on 1, 2 or more of the block faces (see FIG. 3). On the blocks having the preferred slim, flat, rectangular shape, four faces are so narrow that grooves would not be practical to make. Therefore, on such blocks, usually only one or two faces (14,16) bear grooves; these are the two largest opposed faces of the block (Faces A and B in FIG. 8). Depending on how one intends to place the block in ones' closet, grooves on the second face may or may not be desirable.

The hanging means in the cedar block assembly are tightly engaged to the block where the hanging means is a hook 12, it may be engaged by snugly fitting one end of the hook in a hole in the block. Alternatively, the hook may be glued to the block. Where the hanging means is a flexible material as of string or a strap, it is desirable that the string or strap be of adjustable length so that the height of the cedar block assembly in the closet is adjustable.

The cedar block assembly is made as follows. In making the block any order of the following four steps may be used. The steps are cutting out the block from block material stock; shaping the cut stock into a desirable appearance as by rounding or beveling its edges; scoring one or more faces of the block with grooves; and affixing hanging means to the block.

All of the steps may be performed with conventional hand- or mechanized-tools and methods.

The cedar block assembly is used by hanging the assembly in proximity to clothes which are to be protected (or scented). The assembly may be hung from a clothes closet bar, a clothes valet or rack, from the edge of a box, tray, drawer or shelf. The assembly may be hung between garments on hangers suspended from a clothes closet bar as in FIG. 9. The assembly may also be hung over, in front, or behind garments which are suspended from such a bar as in FIG. 10. It may also be laid in a shelf or drawer between shirts or sweaters.

The benefit of the present cedar block assembly may be localized in one's clothes closet by adjusting the position of the assembly with respect to particular garments or parts of garments. This may be done as mentioned briefly above, with adjustable hanging means. It may also be done by placing the assembly either between or in front or behind garments, as shown in FIG. 9. When the assembly having grooves on its observe and reverse faces, it is located between garments A and B. Movement of either garment in the direction of the arrows generates friction which tends to keep the block in contact with both garments. Thus, where one wishes to localize benefit from the assembly between two garments and assembly having the grooves on two opposed faces are suitable.

One may alternatively localize the benefit of the cedar block assembly to two or more garments or parts thereof with assembly having grooves on only one face. Thus, in FIG. 10, one sees an assembly hung behind garments D and E. The grooves on the face of the block are in contact with garments D and E, such that movement of either garment in either direction along the clothes bar tends to retain the block in contact with the other garment.

I claim:

1. A cedar wood oil containing block comprising a solid unitary wooden block suffused with cedar wood oil, at least one surface of said block bearing a plurality of grooves of width between 1 mm and 10 mm.

2. A block according to claim 1, wherein the block is made of cedar wood.

3. A block according to claim 1, wherein the block has at least one flat rectangular surface.

4. A block according to claim 3, wherein the block has two garment-confrontable major surfaces all remaining block surfaces being minor, at least one said garment-confrontable major surfaces bearing grooves parallel to one another.

5. A block according to claim 4, where the block has grooves on only one of said garment-confrontable major surfaces.

6. A block according to claim 1, where the block is substantially spherical and the planes of the grooves are mutually parallel and perpendicular to a predetermined axis.

7. A block according to claim 4, where the block has grooves on both garment-confrontable major surfaces.

8. An assembly comprising a block according to claim 1, and a hanging means affixed to said block which allow said block to be placed and maintained in proximity to garments to insect repellency.

9. A block according to claim 3, having major and minor surfaces wherein one of said major surface comprises at least 1/6 of the entire surface area of the block.

* * * * *